United States Patent [19]

Knust et al.

[11] 4,323,547
[45] Apr. 6, 1982

[54] LABELED FATTY ACIDS AND METHOD OF MAKING AND USING SAME

[75] Inventors: Ernst J. Knust, Jülich; Christiane Kupfernagel, Aachen; Gerhard Stöcklin, Jülich, all of Fed. Rep. of Germany

[73] Assignee: Kernforschungsanlage Jülich GmbH, Jülich, Fed. Rep. of Germany

[21] Appl. No.: 52,965

[22] Filed: Jun. 28, 1979

[30] Foreign Application Priority Data

Jun. 29, 1978 [DE] Fed. Rep. of Germany ....... 2828623

[51] Int. Cl.$^3$ ............... A61K 43/00; A61K 49/00; G01T 1/00
[52] U.S. Cl. ........................................ 424/1
[58] Field of Search .............. 424/1, 9, 311, 312; 128/659, 668; 260/398, 413

[56] References Cited

PUBLICATIONS

Machulla et al., Proc. XIV Int. Ann. Meeting Soc. Nucl. Med., Berlin, Sep. 15-18, 1976.
Freundlieb et al., Proc XV Int. Ann. Meeting Soc. Nucl., Med., Groningen, 13-16, Sep. 1977.
Karim et al., J. Labelled Comp. Radiopharm., vol. XIII, 519 (1977).
Kleijn et al., RadioChem., Radio NKL Letters, 23, 139 (1975).
Robinson, Jr., Radiopharmaceuticals and Labelled Compounds, vol. I, IAEA, Vienna, pp. 423-432 (1973).
Poe et al., Proc. Soc. Exp. Biol. Med., 148, 215-218 (1975).

*Primary Examiner*—Benjamin R. Padgett
*Assistant Examiner*—Christine M. Nucker
*Attorney, Agent, or Firm*—Karl F. Ross

[57] ABSTRACT

Radioactive-halogen labeled fatty acids, especially fatty acids having as an ω-terminal or mid-chain substituent $18_F$ as the labeling atom. The hydrocarbon has more than fifteen carbon atoms in the hydrocarbon chain and is purified by high pressure liquid chromatography for use in investigating the kinetics of material exchange in the heart muscle.

15 Claims, No Drawings

LABELED FATTY ACIDS AND METHOD OF MAKING AND USING SAME

FIELD OF THE INVENTION

The present invention relates to fatty acids labeled with radioactive isotopes, to a method of making such labeled fatty acids, to a method of using such fatty acids and to a method of investigating the kinetics of heart muscle material exchange, i.e. myocardial metabolism.

BACKGROUND OF THE INVENTION

It is known to study the metabolism or material exchange of fatty acids in the heart muscle of human and animal subjects in vivo α-halogenated fatty acids labeled with $^{34m}Cl$, $^{77}Br$ and $^{123}I$, and with $\omega$-$^{77}Br$- or $\omega$-$^{123}I$-labeled fatty acids (see Ma-CHULLA et al, *Preparation, Quality Control and Stability of $^{11}C$, $^{34m}Cl$ $^{77}Br$ and $^{123}I$ labeled Fatty Acids for Heart Muscle Metabolism Studies*, Proc. XIV, International Annual Meeting of the Society of Nuclear Medicine, Berlin, 15–18 September 1976).

The results of such efforts have led to a clinical use of the 17-$^{123}I$-heptadecanoic acid for the in vivo diagnosis of myocardial material exchange (see FREUNDLIEB et al, *Use of 17-$^{123}I$-labeled Heptadecanoic Acid for Noninvasively Measuring Myocardic Metabolism,* Proc. XV International Annual Meeting of the Society of Nuclear Medicine, Groningen, 3–16 September 1977).

The analogous $^{18}F$-labeled acids were probably not considered applicable for such myocardial studies, because of their presumed high toxicity, especially with even numbers of carbon atoms. Also, the pickup of the labeled acid by the heart muscle was found to increase from member to member along the series $\omega$-chloro, $\omega$-bromo- and $\omega$-iodo-labeled acids with the best pickup being found with the latter.

Surprisingly, we have found that the maximum pickup of certain $\omega$-F-fatty acids is greater than that of $\omega$-iodo-fatty acids: with $\omega$-$^{18}F$-heptadecanoic acid a rapid pickup of a maximum of about 40%/g heart is found with heart muscle.

This advantageous maximum pickup, whose magnitude is comparable to that of 1-$^{11}C$-labeled fatty acids, is accompanied by a delayed elimination as is desired for radiographic studies so that these $\omega$-$^{18}F$-labeled fatty acids are especially advantageous for myocardial investigations.

The toxicity usually associated with fluorinated compounds can be countered effectively by the use of these compounds in carrier-free preparations.

The $\omega$-$^{18}F$-fatty acids are especially advantageous for radiographic studies in part because the $^{18}F$ is a positron emitter with rapid incorporation in conjunction with delayed release, not attainable with various hitherto known preparations.

Because of the advantages of positron-emitting $^{18}F(T_{\frac{2}{3}}=110$ minutes), its use in positron-emission tomography has increased in interest as has the interest in fatty acids labeled therewith. By comparison with $^{11}C$ ($T_{\frac{2}{3}}=20$ minutes) which is also a positron emitter, $^{18}F$ has a much longer half life which can increase the circulation path of $^{18}F$ labeled radiopharmaceuticals by several hundred km.

ROBINSSON: *Biologically Active $^{18}F$-Fluoroorganic Compounds,* Proc.Symp.New Devel.Radiopharm.labeled comp., Copenhagen, Bd.I IAEA, Vienna, p.423 (1973), describes $^{18}F$ substituted fatty acids of a chain length up to 14 carbon atom having the $^{18}F$ substituents in the 2 or α position. Typical of these compounds are the 2-$^{18}F$-fluorohexanoic acid and 2-$^{18}F$-tetradecanoic acids which have been proposed for myocardial investigations.

α-$^{18}F$ labeled fatty acid esters and their production are described in KARIM et al: *Fluorine-18 labeling of Lower Fatty Acids by Heterogeneous Exchange on Gas Chromatographic Columns,* J. Lab. Comp. Radiopharm., 13, 519 (1977).

Heart-muscle tests have shown, as to maximum enrichment in the myocardium, that the α$^{18}$Flouro fatty acids are less effective than the corresponding Cl, Br or I compounds, and far less in the combination of surprising effects described above than the corresponding $\omega$-$^{18}F$ fatty acids.

Another object of the invention is to provide an improved method of investigating heart muscle exchange of radioactive labeled fatty acids.

DESCRIPTION OF THE INVENTION

These objects are attained, in accordance with the present invention, which is based upon our surprising discovery that $\omega$-terminal or centrally labeled $^{18}F$ fatty acids having 10 to 20 carbon atoms in the carbon chain, preferably after purification by high pressure liquid chromatography, are especially effective in the investigations of the kinetics of heart muscle exchanges.

The aforementioned class of compounds excludes the α-$^{18}F$-fatty acids. Preferably the included class is that of $\omega$ and/or midsubstituted $^{18}F$ fatty acids having upwards of 15 carbon atoms in the carbon chain and especially the unsaturated fatty acids of this latter group. The substituent-carrying C atom in the $\omega$ position or a midchain position are preferably monofluorinated.

Excellent results are obtained with the $\omega$-fluorinated ($^{18}F$) $C_{16}$-$C_{18}$-alkanoic acids and the 9 and 10 monofluorinated alkanoic acids of similar chain length. Especially effective results were obtained with the isomaric mixture (9/10)-$^{18}F$-stearic acid.

We have found that a high-speed method of preparation, yielding a product readily susceptible to high pressure liquid chromatography, can be effected by treating the analogous brominated fatty acid with potassium fluoride containing $^{18}F$ to effect halogen replacement and thereupon recovering the organic product and subjecting the same to hydrolysis (saponification).

The reaction is advantageously carried out in a nonaqueous (water-free) acetamide. The replacement of bromine by $^{18}F$ in organic compounds using $K^{18}F$ in nonaqueous acetamide is itself known (sse J.P. deKleijn et al: *$K^{18}F$ from Reactor-Produce Fluorine-18 Syntheses of Ethyl-2-Fluoropropionate-18 F and 4-toluensulfonyl fluoride-$^{18}F$,* Radiochem, Radional. Letters, 23, 139(1975).

Preferably the $K^{18}F$ is produce by the addition of KF to $^{18}F$-containing $H_2O$.

SPECIFIC EXAMPLE

The $K^{18}F$ is formed by the treatment of 1 mg KF with 10 ml $H_2O$, the $^{18}F$-containing water being formed by $^3He$ irradiation and the reaction $^{16}O(^3HeP)$ $^{18}F$. The solution is reduced to 200 microliters by distillation, the residue being introduced into a 3 milliliter quartz ampule, capable of being sealed, by a microliter spray. In this ampule the solution is subjected to evacuation to $10^{-6}$ bar, with slight heating, to dryness. After cooling the solid residue is reacted with 20 mg of the bromine fatty acid methylester of each of the $C_{16}$, the $C_{17}$ and the $C_{18}$ fatty acids in respective tests. 100 mg of acetamide, recrystallized from benzene, also was added to each ampule.

The ampule is sealed in vacuo and then heated for one hour with agitation in a sealed bath to 150° C.

The ampule seal was broken and the ester saponified by boiling the contents of the ampule for one half hour with 2 milliliters methanolic potassium hydroxide (5N) with refluxing.

The ampule was flushed in a shaker vessel of a volume of about 60 milliliters with about 10 milliliters of water.

The contents of the flask were acidified with 3 milliliters of sulfuric acid, diluted 1:6, and extracted three times with n-heptane (first with 10 milliliters and twice with 5 milliliters) at 80° C. The extraction phases were separated by centrifugation.

The combined heptane fractions were evaporated to dryness and the residue taken up with about 2 milliliters of elution medium (described below) and heated.

The $^{18}F$ fatty acid is purified by high pressure liquid chromatography. The chromatography separation was preferably effected by phase-reversal chromatography under the following conditions:

| Chromatograph Column: | Waters<br>Waters, $\mu$-$NH_2$ Bondapak 30 × 0.4 cm |
|---|---|
| Elution medium: | n-heptane/acetic acid = 998/2 |
| Elution medium feed rate: | 3 milliliters per minute |

In the case of 17-$^{18}F$ heptadecanoic acid the radiochemical yield was 30±2% with a specific activity greater than 10 mCi/mg with compact cyclotron production of $^{18}F$ in water by the nuclear reaction $^{16}O(^3He.p)^{18}F$. Similar yield was obtained with the $\omega$-$^{18}F$-palmitic acid. The radiochemical yield of the (9/10)-$^{18}F$ stearic acid was 4%.

Animal experiments with mice were carried out using the product resulting from the high pressure liquid chromatographic purification after evaporation of the eluate to dryness in a rotary evaporator and the dissolution of the product in human serum albumin. The solution is filtered and injected in aliquot portions to the tail vein of each animal.

Animal experiments with NMRI mice, using 16-$^{18}F$ hexadecanoic acid 17-$^{18}F$ hexadecanoic acid and (9,10)-$^{18}F$ stearic acid shows a rapid increase in the $^{18}F$ activity in the heart muscle so that within about two minutes the activity reaches a maximum of about 40% gram (heart). Thereafter, there is a complex dropoff with a short-duration component of two to six minutes and a long-duration component of eighteen to fifty-one minutes.

The activity characteristic can be understood in terms of the beta-oxidation theory of fatty acids, whereby the fatty acids after their rapid extraction through the heart muscle are initially decomposed to acetyl-coenzyme A and a lower $^{18}F$ carboxylic acid which is discharged as such or becomes involved in the citric acid cycle in which further metabolism occurs.

Apart from its deposition in the heart muscle, $^{18}F$ labeled fatty acid is also found in the liver, lungs, kidneys, stomach, bowels and blood as detected by the increase in $^{18}F$ activity therein. The differences in activity in the upper thigh for the three fatty acids mentioned above, signify that slightly different metabolism and deposit mechanisms may be involved for them.

Comparisons of the results obtained with the $^{18}F$ labeled fatty acids of the present invention and $^{123}I$ fatty acids corresponding thereto, show significant improvement in the takeup and discharge of the labeled materials and improved effectiveness in the noninvasive study of heart muscle exchange.

The following table assembles the results of comparative tests with the compounds of the invention and prior art compounds:

| Fatty Acid | Max: Enrichment in % of Injected Dose per Heart | Time to Max. Enrichment[min] | Elimination [min] rapid elimination | Half-time slow elimination |
|---|---|---|---|---|
| 1-[$^{11}C$]Palmitic acid | $3.8_7 \pm 1.0$ | 0.25 | $0.4 \pm 0.1$ | $33 \pm 6.5$ |
| 16-$^{123}I$-Palmitic acid | $3.3_6 \pm 0.4$ | 0.5 | $2.4 \pm 0.5$ | $33 \pm 6.6$ |
| 17-$^{123}I$-Heptadecanoic acid | $3.9_7 \pm 0.4$ | 0.25 | $2.1 \pm 0.4$ | $25 \pm 5.0$ |
| 17-$^{77}Br$-Heptadecanoic acid | $2.2_{10} \pm 0.6$ | 0.5 | $0.6 \pm 0.1$ | $36 \pm 7.2$ |
| 17-$^{34m}Cl$-Heptadecanoic acid | $2.1_6 \pm 0.6$ | 0.25 | $0.9 \pm 0.2$ | $23 \pm 4.7$ |
| 16-$^{18}F$-Palmitic acid | $4.3_5 \pm 1.3$ | 0.25 | $3 \pm 0.8$ | $44 \pm 11$ |
| 17-$^{18}F$-Heptadecanoic acid | $4.8_{12} \pm 0.8$ | 0.5 | $6 \pm 1.5$ | $18 \pm 6$ |
| 9/10-$^{18}F$-Stearic acid | $4.2_5 \pm 0.9$ | 0.5 | $4 \pm 1$ | $24 \pm 7$ |
| 2-$^{123}I$-Stearic acid | $1.4_{11} \pm 0.1$ | 0.5–1 | $2 \pm 0.4$ | $13 \pm 2.7$ |
| 2-$^{77}Br$-Stearic acid | $1.4_7 \pm 0.3$ | 1 | $1 \pm 0.2$ | $18 \pm 3.6$ |
| 2-$^{34m}Cl$-Stearic acid | $2.0_3 \pm 0.1$ | 1 | $0.9 \pm 0.2$ | $9 \pm 1.8$ |
| 2-$^{18}F$-Stearic acid | $1.3_4 \pm 0.1$ | 1 | $0.5 \pm 0.1$ | $5 \pm 1.5$ |

We claim:

1. An $^{18}F$ labeled fatty acid, particularly for investigation into the kinetics of heart muscle metabolism containing at least one positron-emitting $^{18}F$ atom at the $\omega$ terminal or at least at one position along the chain substantially central of the $\alpha$ and $\omega$ terminals.

2. An $^{18}F$ labeled fatty acid defined in claim 1 having 10 to 20 carbon atoms in the carbon chain.

3. The $^{18}F$ labeled fatty acid defined in claim 2 which is unsaturated and has at least 15 carbon atoms.

4. The $^{18}F$ labeled fatty acid defined in claim 2 which has 16, 17 or 18 carbon atoms.

5. In a method of investigating heart muscle metabolism by a noninvasive process, the improvement which comprises administering to the subject an $^{18}F$ labeled fatty acid as defined in claim 1.

6. The improvement defined in claim 5 wherein the $^{18}F$ labeled fatty acid is subjected to high pressure liquid chromatographic purification prior to administration to the subject.

7. The improvement defined in claim 6 wherein the $^{18}F$ labeled fatty acid has an uneven number of carbon atoms.

8. The improvement defined in claim 4 wherein the $^{18}F$ labeled fatty acid is selected from the group which consists of 16-$^{18}F$ hexanoic acid, 17-$^{18}F$ heptadecanoic acid and (9,10)-$^{18}F$ stearic acids.

9. A method of making the compound defined in claim 1 which comprises the steps of reacting potassium fluoride containing $^{18}F$ and an ester of the analogous brominated fatty acid in halogen exchange to produce a reaction product, and hydrolyzing the reaction product.

10. The method defined in claim 9 wherein the reaction is carried out in water free acetamide.

11. The method defined in claim 9 wherein the potassium fluoride is produced by treating KF with $^{18}F$ containing ester and evaporating the resulting mixture to dryness.

12. The method defined in claim 11, further comprising the step of purifying the $^{18}F$ labeled fatty acid by high pressure liquid chromatography.

13. A composition of matter for noninvasive investigation of heart-muscle metabolism processes, comprising the product of claim 12.

14. The composition defined in claim 13 wherein the $^{18}F$ labeled fatty acid is selected from the group which consists of 16-$^{18}F$-palmitic acid, 17-$^{18}F$-heptadecanoic acid and (9/10)-$^{18}F$-stearic acids.

15. The composition defined in claim 13 or claim 14 which further comprises a human serum albumin solution as a vehicle for said $^{18}F$ labeled fatty acid.

* * * * *